United States Patent [19]

Mackie

[11] Patent Number: 4,920,993
[45] Date of Patent: May 1, 1990

[54] DENTAL FLOSS APPLICATOR FOR FLOSSING TEETH

[76] Inventor: Kenneth H. Mackie, P.O. Box 36086, Pensacola, Fla. 32516

[21] Appl. No.: 251,769

[22] Filed: Oct. 3, 1988

[51] Int. Cl.$^5$ ............................................. A61C 15/00
[52] U.S. Cl. ...................................... 132/324; 132/323
[58] Field of Search ............... 132/323, 324, 325, 326, 132/327

[56] References Cited

U.S. PATENT DOCUMENTS

| | | | |
|---|---|---|---|
| 2,450,635 | 10/1948 | Dembenski | 132/325 |
| 3,747,611 | 7/1973 | Bennington | 132/325 |
| 3,861,406 | 1/1975 | Stitt | 132/325 |
| 3,929,144 | 12/1975 | Tarrson et al. | 132/323 |
| 4,005,722 | 2/1977 | Bragg | 132/324 |
| 4,133,339 | 1/1979 | Naslund | 132/323 |
| 4,518,000 | 5/1985 | Leverette | 132/325 |
| 4,597,398 | 7/1986 | Chu | 132/324 |
| 4,657,034 | 4/1987 | Koski | 132/324 |

*Primary Examiner*—John Weiss
*Assistant Examiner*—Andriene Lepiane
*Attorney, Agent, or Firm*—E. Lieberstein

[57] ABSTRACT

This invention relates to a dental floss applicator for flossing teeth with dental floss supplied from the applicator. More particularly, the present invention relates to a dental floss applicator for dispensing dental floss and for securing a pre-selected length of dental floss between a supply and take up unit to permit the flossing of teeth without hand contact in the mouth.

11 Claims, 3 Drawing Sheets

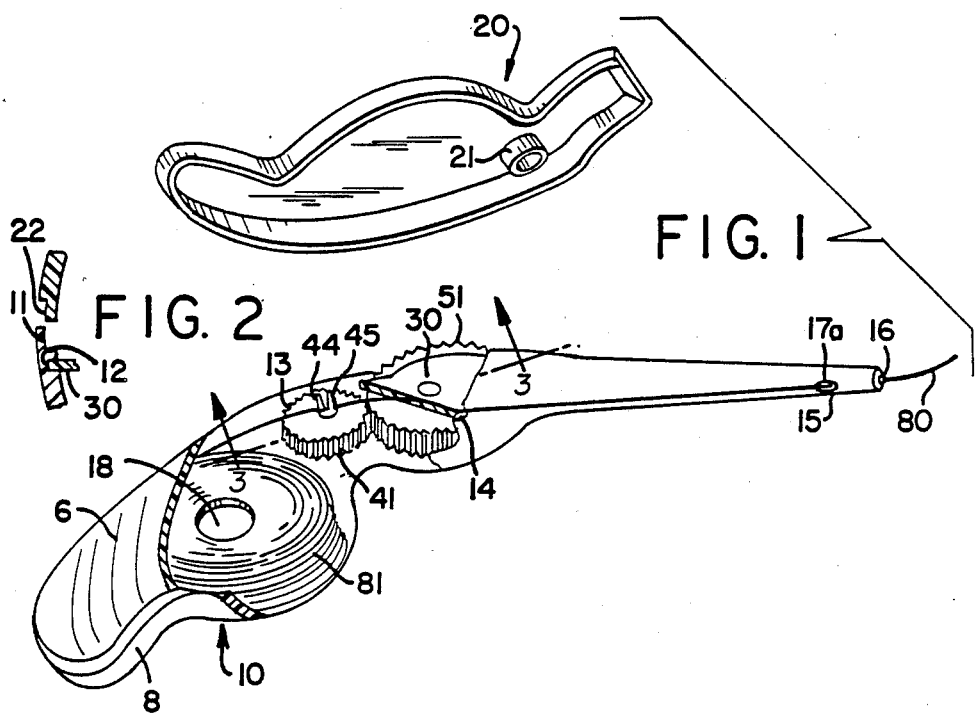
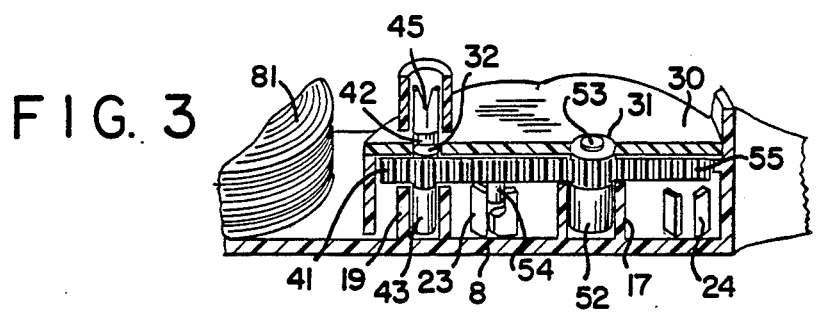
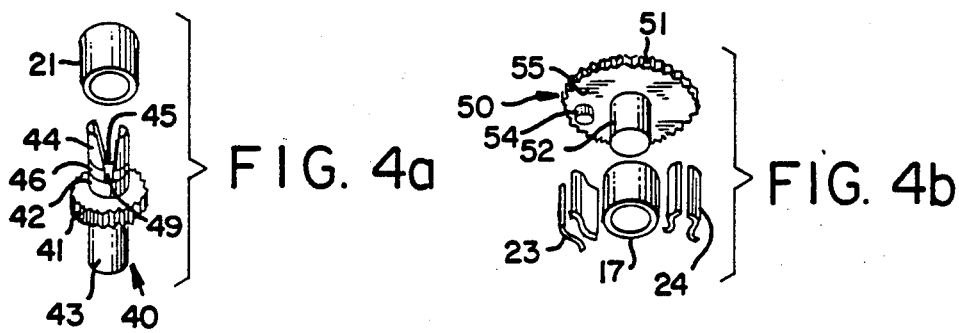

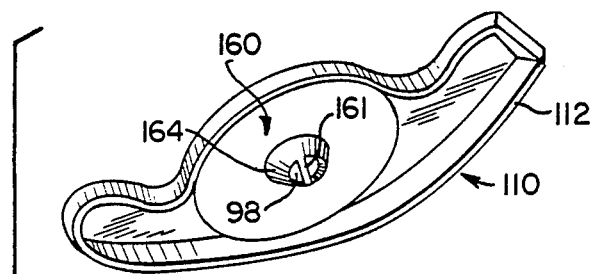
FIG. 5
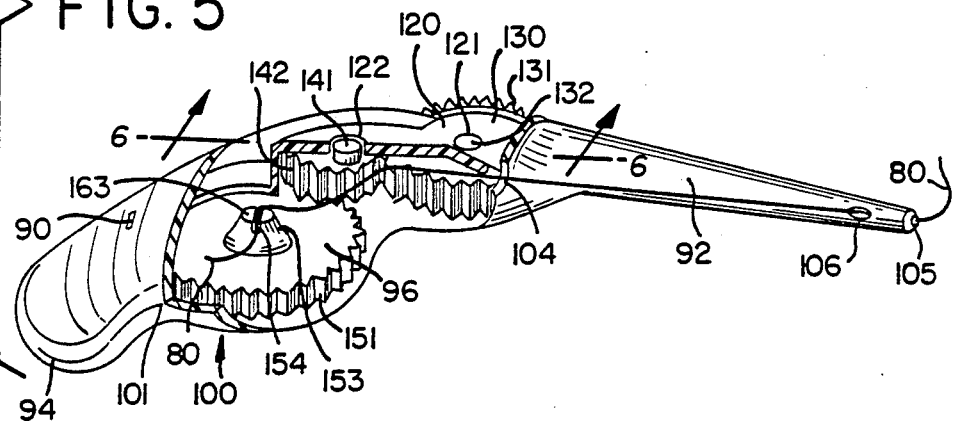
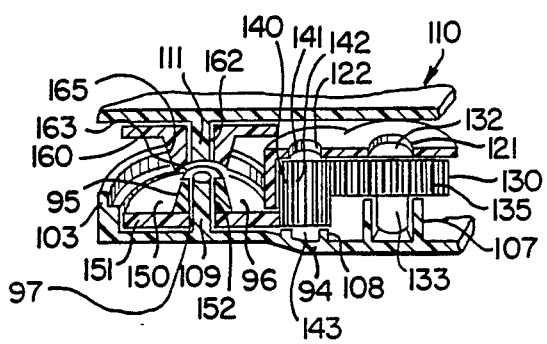
FIG. 6
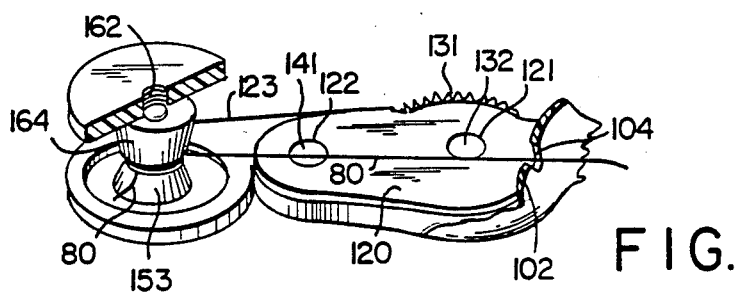
FIG. 7

DENTAL FLOSS APPLICATOR FOR FLOSSING TEETH

BACKGROUND OF INVENTION

Dental floss is used to clean the interproximal spaces between adjacent teeth and for massaging the gums at the interproximal. Many dental floss applicators have been commercially marketed as a sanitary substitute for otherwise using one's fingers to hold a short length of floss between two hands. Dental floss is composed of a twisted multi-strand material composite which readily frays during use and is easily broken unless carefully applied. The dental applicators currently on the market do not permit dental floss to be controllably unwound from a supply roll in such a way that a short, pre-selected length of dental floss may be dispensed and locked to hold a pre-selected length under tension during flossing. In addition, dental floss applicators currently marketed are not adaptable for use with orthodontic braces and have minimal utility for flossing fixed permanent bridges in situ within the mouth.

SUMMARY OF THE INVENTION

The preferred embodiment of the invention is a dental floss applicator comprising a dental floss dispensing unit, including a supply spool for storing a line of dental floss, a manually operated gear and lock assembly having one position for adjustably releasing said line of dental floss from said supply spool and another position for locking said line of dental floss in an immobile position and a separate dental floss take-up unit comprising a take-up member for storing dental floss dispensed from said dispensing unit and means for controllably winding said take-up member with said dispensing unit and take-up unit adapted to be held in separate hands. A removable adapter for the dispensing unit permits the dispensing unit to be operated independent of said take-up unit for flossing orthodontic braces and permanent bridges.

In accordance with another embodiment of the present invention, the dental applicator broadly comprises a dispensing unit adapted to be held in one hand including a supply spool for storing a line of dental floss, a manually operated gear assembly having a thumb wheel control, a lock assembly connected to said gear assembly and being responsive to the position of said thumb wheel for releasably locking said line of dental floss to prevent dispensing dental floss from said supply spool when said thumb wheel is rotated into a first position and for unlocking said line of dental floss so as to freely permit dental floss to be unwound from said supply spool when said thumb wheel is rotated into a second position. The dispensing unit may be used in conjunction with a second free hand of the operator, although the preferred operation is to use the dispensing unit in conjunction with a take-up unit containing a take-up member about which dental floss supplied from the dispensing unit is wound and a manually operated gear assembly for controlling the operation of the take-up member.

The present invention further includes an adapter for use in conjunction with the dispensing unit of the dental applicator to permit flossing of orthodontic braces and permanent bridges. The adapter includes means for mounting the adapter upon one end of the dispensing unit and an elongated member extending transversely to the end of the dispensing unit upon which the adapter is mounted, with the elongated member having a distal end and an opening at the distal end thereof through which the line of dental floss is threaded.

BRIEF DESCRIPTION OF THE DRAWINGS

Other advantages of the present invention will become apparent from the following detailed description of the invention when read in conjunction with the following drawings of which:

FIG. 1 is a perspective view of the dental floss dispensing unit of the present invention with part of the cover shown removed from the body of the unit to expose the internal components of the dispensing unit;

FIG. 2 is a side cross section of the dispensing unit of FIG. 1 for showing how the cover locks into the body of the unit;

FIG. 3 is a view of the dental floss dispensing unit shown partially in cross section and partially in perspective taken along the lines 3—3 of FIG. 1;

FIG. 4A is an exploded perspective of the manually operated gear assembly of FIG. 3, and FIG. 4B is an exploded perspective of the manually operated lock assembly of FIG. 3;

FIG. 5 is a perspective view of the dental floss take-up unit of the present invention with the cover shown removed from the body of the take-up unit to expose the internal components of the take-up unit;

FIG. 6 is a view of the dental floss take-up unit shown partially in cross section and partially in perspective taken along the lines 6—6 of FIG. 5;

FIG. 7 is a perspective view of the take-up spool assembly for the take-up unit of FIG. 5;

DETAIL DESCRIPTION OF THE INVENTION

Figure 8:
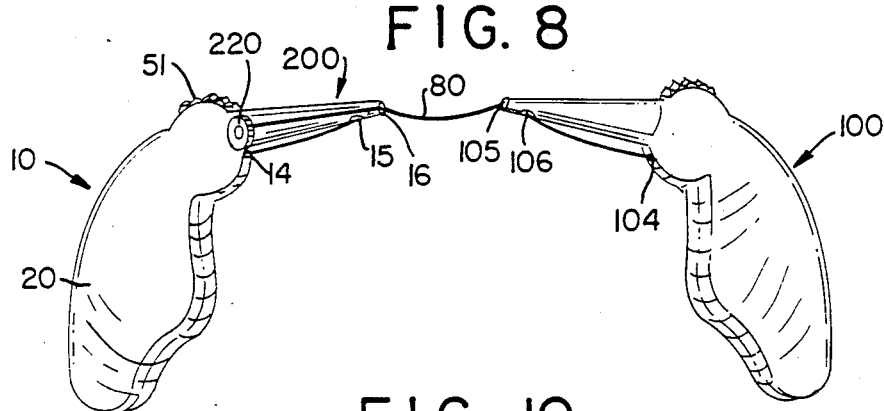
FIG. 8 is a perspective of the dispensing unit and the take-up unit in a fully operational mode.

Referring to FIGS. 1 to 4, which illustrate the dental floss dispensing unit (10) of the present invention with part of the cover (20) of the unit (10) removed to expose the operating components of the dispensing unit (10). The dispensing unit (10) is shaped in a configuration with a handle portion (6) and an elongated conically-shaped front end (7) forming a finger-like projection extending from the handle portion (6). The unit (10) is molded into two sections, including a removable cover (20) and a lower body (8). The cover (20) has a depending lip (22), as shown in FIG. 2, which interlocks into a corresponding notch (11) in the lower body (8) for attaching the two sections together. The lower body (8) is molded to form a container for supporting a supply spool (81) about which is wound a strand (80) of dental floss of any conventional composition. The spool (81) is rotatably mounted upon a post (18) extending upright from the body (8), permitting the strand (80) to be freely unwound from the spool (81).

A gear assembly (50) is mounted in the unit (10) between the lower body (8) and a support plate (30). The support plate (30) is horizontally aligned in the unit (10) above the gear assembly (50) and locks into a notch (12) formed in the lower body (8) beneath notch (11), as shown in FIG. 2. The gear assembly (50) includes a manually operated drive gear (55) having gear teeth (51) and an idler gear (41) which is driven by the drive gear (55). The drive gear (55) is manually operated, preferably with the thumb of the hand against the gear teeth (51). The drive gear (55) has a shaft (52) which is rotatably supported in a cylindrical bearing (17) extending from the lower body (8). The shaft (52) of the drive gear (55) is also rotatably supported in an opening (31) in the support plate (30). The gear teeth (51) protrude through a slot formed in the lower body (8) to provide access to the gear teeth (51) external to the unit (10). In this way, the thumb of the hand holding the unit (10) may operate the gear assembly (50).

The idler gear (41) has a shaft (43) in symmetrical alignment with shaft (52) of drive gear (55). The shaft (43) is rotatably supported in a cylindrical bearing (19) extending from the lower body (8). The shaft (43) also extends through an opening (42) in the support plate (30) to form an extension (44) which lies between the support plate (30) and the cover (20). The extension (44) is bifurcated and beveled to form a slot (45) with a fork-like shape. A groove (46) is formed around the extension (44) approximate the apex (49) of the slot (45). The beveled slot (45) operates in conjunction with the idler gear (41) to function as the locking assembly (40) of the present invention for holding the strand (80) of dental floss in an immobile position when the drive gear (55) is rotated into a locked position, as will be explained hereafter.

A detent pin (54) extends from the drive gear (55). A pair of detents (23) and (24) extend from the lower body (8) on opposite sides of the cylindrical bearing (17) for releasably engaging the detent pin (54) upon a 180 degree rotation of the drive gear (55) in either direction.

The strand (80) of dental floss is fed from the supply spool (81) above the support plate (30) through the beveled slot (45) and passed out of the unit through an opening (14) from whence then strand (80) is directed outside the unit (10) along the length of the conically-shaped front end (7) and re-threaded into the unit (10) through an opening (15) near the front face (16). The strand (80) of dental floss is then passed into an internal bore (17a) in the front end (7) from where it exits the unit (10). Alternatively, the strand (80) may be fed internal of the unit (10) through the bore (17a) in the conically-shaped front end (7) so as to exit from the front face (16) of the unit (10).

Operation of the dispensing unit (10) is carried out by rotating the drive gear (55) using the thumb of one hand in contact with the gear teeth (51). The drive gear (55) is rotated from a position with the detent pin (54) in one of the detents (23) or (24) until the drive gear detent pin (54) is rotated into engagement with the other. Rotation of the drive gear (55) in the forward direction rotates the idler gear (41), which, in turn, rotates the extension (44), causing the strand of floss (80) extending through the slot (45) to wrap itself around the groove (46). This locks the strand of floss and prevents further release of floss from the supply spool (81). The shield plate (30) isolates the strand (80) of dental floss from the gear assembly (50) and protects dental floss from becoming entangled in either the drive and/or idler gears of the gear assembly (50). The dental floss is unlocked by rotating the drive gear (55) in the opposite direction. When the drive gear detent pin (54) is rotated back into engagement with the detent pin (23), representing the unlocked position, the strand (80) of dental floss wound around groove (46) is unwound. The strand (80) of dental floss forming supply spool (81) may then be freely pulled out of the unit (10). The cover (20) of the unit (10) has a dental floss lock guide (21) in the form of a cylindrical shell which extends from the cover (20) and fits over the bifurcated slot (45) to assure that the strand (80) of dental floss stays in position in the slot (45) when the locking assembly (40) is in the unlocked position.

Although the dental floss applicator of the present invention may consist only of a dispensing unit (10), it is preferred to use the dispensing unit (10) in conjunction with a take-up unit (100) adapted to be held in the opposite hand. The take-up unit (100), as shown in FIGS 5–7, is of a generally identical configuration to that of the dispensing unit (10) and includes a handle portion (90) and an elongated conically-shaped front end (92) which forms a finger-like projection extending from the handle portion (90). The unit (100) is molded into two sections represented by a lower body (94) and a cover (110). A take-up spool (150) in the unit (100) is used to collect used dental floss dispensed from the unit (10). The take-up spool (150) includes a lower section (153) and an upper section (164). The lower section (153) has a conically shaped body (95) extending from a gear plate (96), with an opening (97) extending through the gear plate (96) and body (95). A slot (154) is formed in the lower section (153) for engaging a drive bar (161) in the upper section (164). The upper section (164) has an inverted conically-shaped body (165), complementary to body (95), extending from the cover (110) with a cylindrical bore (98). The drive bar (161) is located in the bore (98). When the cover (110) is fitted over the lower body (94), the bore (98) in the upper section (164) fits over the upper end (163) of the lower section (153) and the drive bar fits into the slot (154). The conically-shaped lower section (153) and the conically-shaped upper section (164) of the take-up spool (150) are inverted geometrically to form an hourglass-like shape for collecting used dental floss.

The gear plate (96) is rotatably mounted upon a post (109) extending from the lower body (94). The take-up spool 150) is controlled by a drive gear assembly (130), including a manually operated drive gear (135), an intermediate idler gear (140), and the gear plate (96). The drive gear assembly (130) is supported in the lower body (94) of the take-up unit (100) and is separated from the cover (110) by a support plate (120). The manually operated drive gear (135) has a section of gear teeth (131) extending through an opening in the lower body (94) to provide access for operating the drive gear (135) manually and preferably with the thumb of the hand. The gear teeth (131) engage the gear teeth (142) of the idler gear (140) which, in turn, engage the gear teeth (151) of the gear plate (96. The drive gear (135) has a shaft (133) supported in a cylindrical bearing (107) extending from the lower body (94). The shaft (133) also extends through a hole (121) in the support plate (120). The idler gear (140) has a shaft (143) supported in a cylindrical bearing (108) extending from the lower body (94) in symmetrical alignment with shaft (133).

In operation, the thumb of the hand holding the take-up unit (100) contacts and rotates gear teeth (131) rearward thereby rotating gear assembly (130). The drive gear (135) in the gear assembly (130) causes the idler gear (140) to rotate which, in turn, rotates gear plate (96), thereby rotating the take-up spool (150).

To insert dental floss into the take-up unit (100), the strand (80) of dental floss from the dispensing unit (10) is inserted into the floss tip entrance hole (105) in the front end section (92) of the take-up unit (100). The strand (80) is then passed out of the unit (100) through the hole (106) and along the length of the front end section (92) of the unit (100) where it is fed back into the unit through the hole (104). With the cover (110) lifted off the unit (100), the strand (80) is pulled over the support plate (120) and threaded through slot (154) of the take-up spool (150). The strand (80) of dental floss may be wrapped one or two turns around the lower section (153) before the cover (110) is re-attached to the lower body (94). The edge (112) of the cover (110) preferably snaps into a notch (not shown) in the lower body (94) in a manner similar to FIG. 2. Used dental floss is drawn into the take-up unit by manually rotating the thumb wheel gear teeth (131). By appropriate sizing of the gears, the dental floss (80) will not withdraw from the take-up unit (100), unless the drive gear (135) is deliberately rotated forwards.

Figure 9:
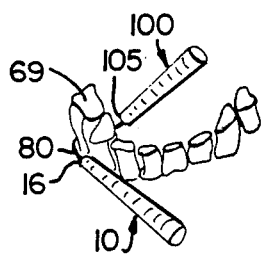
FIG. 9 is a diagrammatic view in perspective of the dispensing unit and take-up unit of FIG. 8 shown in use for performing a normal flossing operation between teeth.

The dispensing unit (10) and the take-up unit (100) are preferably operated together, as shown in FIG. 8, with each held in opposite hands and with a minimum length of dental floss (80) held tautly between the units. The dispensing unit (10) should be operated with the gear assembly in the locked position. To floss normal teeth, no adapter or tip attachment is required. The strand (80) of dental floss is held horizontally between the unit (10) and the unit (100) as shown in FIG. 9 using a sawing motion to floss between the teeth.

FIGS. 10-14 illustrate various adapters to attach to the dispensing unit (10) for flossing orthodontic braces and/or permanent bridges.

Figure 10:
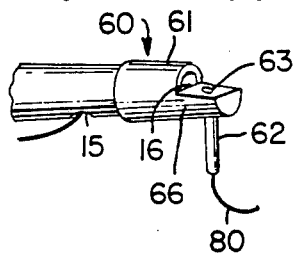
FIG. 10 is a perspective view of an adapter for the dispensing unit of FIG. 1, preferably for flossing orthodontic bridges.
Figure 11:
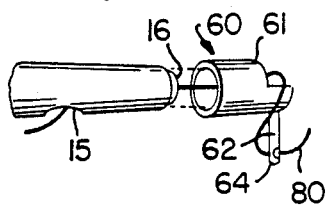
FIG. 11 is a perspective view of an adapter for the dispensing unit of FIG. 1 for flossing orthodontic bridges.
Figure 12:
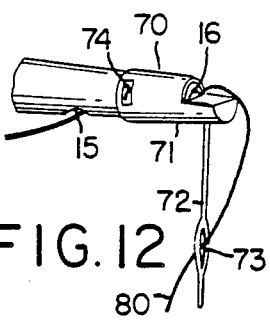
FIG. 12 is a perspective view of a modified adapter of FIG. 10 for flossing permanent bridges.

The adapter (60), shown in FIG. 10, has a hollow barrel-shaped body (61) adapted to be mounted over the front face (16) of the front end portion (7) of unit (10) and a semi-spherical extension (66) which forms a lip for directing the strand (80) of dental floss withdrawn from the unit (10). In the embodiment of FIG. 10, the strand (80) of dental floss is fed through a cavity (63) in the extension (66) and through a tube (62) which lies transverse to the front end portion (7) of the unit (10). Alternatively, the tube (62), as shown in FIG. 11, can be solid with an opening (64) at the distal end thereof through which the strand (80) is threaded. For use with a permanent bridge, the tube extending from the flexible material adapter is preferably in the form of a thin needle (72), as shown in FIG. 12, having an opening (73) at its distal end through which the strand (80) is threaded. In the embodiment of FIG. 10, the strand of dental floss is fed through the tube (62), whereas in the embodiments of FIGS. 11 and 12, the strand (80) is threaded through the opening (64) and (73) at the distal end of the tube, respectively.

Figure 13:
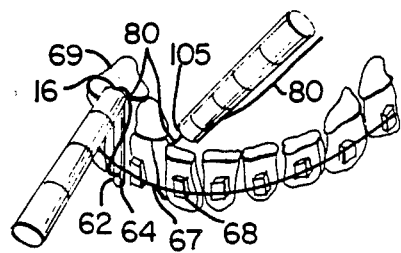
FIG. 13 is another diagrammatic view in perspective showing the flossing operation with the adapter of FIG. 10 or FIG. 11.

For flossing teeth with an orthodontic brace, as shown in FIG. 13, the adapter (60) of FIG. 10 or of FIG. 11 is mounted over the front face (16) of the unit (10) and the strand (80) of dental floss is passed through the adapter (60) and through the bore of the tube (62) or is threaded through the opening (64) and then fed into the take-up unit (100) as explained heretofore. The tube (62) is placed between an orthodontic wire (67) and the teeth with an orthodontic clip (68) separating the tube (62) from the teeth. Tension is increased on the strand (80) of dental floss by separating the units (10) and (100) and adjusting the gear teeth (131) in the take-up unit (100). With a simultaneous pressing and sawing motion, the strand (80) of dental floss passes through the gap between the adjacent teeth. Flossing is then accomplished in a normal manner.

Figure 14:
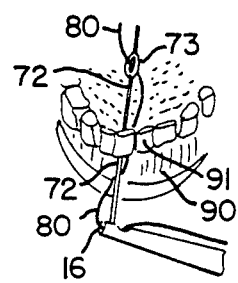
FIG. 14 is yet another diagrammatic view in perspective showing the flossing operation with the adapter of FIG. 12.

The adapter (70), shown in FIG. 12, is preferred for use in flossing a permanent bridge. It is also preferred when flossing a permanent bridge that the dispensing unit (10) be used without the take-up unit, i.e., the strand (80) of dental floss passing through the opening (73) of the needle (72) should be held in a free hand. The adapter (70) includes a floss cutter (74) for severing off excess dental floss. The needle (72) is placed between the gums (90) of the dental patient and the permanent bridge (91), as shown in FIG. 14. The operator unlocks the gear assembly (50) and holds the strand (80) of dental floss in the free hand while withdrawing the unit (10) and the needle (72) from the bridge (91). The gear assembly (50) is then relocked and the bridge is flossed with the strand (80) of dental floss between the free hand and the unit (10). After flossing, the strand (80) of dental floss is withdrawn and the used portion is severed and discarded.

Although the various types of adapters (60) and (70) are shown as separate units, an adapter may be integrated into the unit to form part of the dispenser (10).

What is claimed is:

1. A dental floss applicator for dispensing floss and for flossing teeth, comprising: a dispensing unit adapted to be held in one hand, including a supply spool for storing a line of dental floss, a manually operated gear assembly having a thumb wheel control, a drive gear and an idler gear and a lock assembly connected to said idler gear with said lock assembly being responsive to the position of said thumb wheel for releasably wrapping a section of said line of dental floss into a locked position to prevent dispensing dental floss from said supply spool when said thumb wheel is rotated into a first position and for unwrapping said line of dental floss from said locked position so as to freely permit dental floss to be unwound from said supply spool when said thumb wheel is rotated into a second position.

2. A dental floss applicator, as defined in claim 1, further comprising a dental floss take-up unit adapted to be held in a separate hand from said dispensing unit, with said take-up unit comprising a take-up member for storing dental floss dispensed from said dispensing unit and for permitting teeth to be flossed with the dental floss held in tension between the dispensing unit and the take-up unit and means for controllably winding said take-up member.

3. A dental floss applicator, as defined in claim 2, wherein said means for controllably winding said take-up member comprises a drive gear assembly, including a drive gear having a thumb wheel control, an idler gear and a gear plate coupled to said take-up member.

4. A dental floss applicator, as defined in claim 1, wherein said drive gear has gear teeth extending from said dispensing unit representing said thumb wheel control.

5. A dental floss applicator, as defined in claim 4, wherein said lock assembly comprises means having a slot extending therethrough for receiving said line of dental floss and means connected to said idler gear so that upon rotation of said thumb wheel, said idler gear rotates said slot for locking or unlocking the line of dental floss.

6. A dental floss applicator, as defined in claim 5, wherein said means having a slot is a bifurcated member in the form of a fork which is connected to said idler gear.

7. A dental floss applicator, as defined sin claim 5, further comprising adaptor means for use in combination with said dispensing unit for flossing teeth with orthodontic braces or a permanent bridge, wherein said adaptor means comprises guide means extending from said dispensing unit for guiding the line of dental floss discharged from said dispensing unit and a thin, elongated member extending transversely of said guide means for redirecting said line of dental floss in a direction transverse to said guide means.

8. A dental floss applicator, as defined in claim 7, wherein said thin, elongated member is a solid, cylindrical tube having a distal end opposite said guide means and an opening approximate said distal end, with said line of dental floss threaded through said opening.

9. A dental floss applicator, as defined in claim 7, wherein said thin, elongated member is a needle having a distal end opposite said guide means and an opening approximate said distal end, with said line of dental floss threaded through said opening.

10. A dental floss applicator, as defined in claim 7, wherein said thin, elongated member is a hollow tube through which said line of dental floss is directed.

11. A dental floss applicator, as defined sin claim 7, wherein said dispensing unit is in a configuration with a handle and a finger-like projection extending from said handle and wherein said adaptor is mounted on said finger-like projection.

* * * * *